(12) United States Patent
Shieh et al.

(10) Patent No.: US 6,653,503 B2
(45) Date of Patent: Nov. 25, 2003

(54) MICROWAVE IRRADIATION PROCESS FOR PREPARING METHYL ESTERS

(75) Inventors: Wen-Chung Shieh, Berkeley Heights, NJ (US); Steven Dell, Madison, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/214,644

(22) Filed: Aug. 8, 2002

(65) Prior Publication Data

US 2003/0144543 A1 Jul. 31, 2003

Related U.S. Application Data

(63) Continuation-in-part of application No. 10/024,055, filed on Dec. 17, 2001, now abandoned.

(51) Int. Cl.$^7$ .............................................. C07C 69/02
(52) U.S. Cl. .............................. 560/231; 560/9; 560/81; 560/105; 560/147; 560/155; 560/179; 560/205
(58) Field of Search .............................. 560/231, 9, 81, 560/105, 147, 155, 179, 205

(56) References Cited

U.S. PATENT DOCUMENTS

| 4,513,146 A | * | 4/1985 | Thompson | 560/231 |
| 5,278,333 A | | 1/1994 | Loosen et al. | 562/52 |

FOREIGN PATENT DOCUMENTS

WO    WO 01/81305    11/2001

OTHER PUBLICATIONS

Kabza et al, J. Org. Chem. 2000, vol. 65 pp. 1210–1214.*
Perreux et al., "A Tentative Rationalization of Microwave Effects in Organic Synthesis According to the Reaction Medium, and Mechanistic Considerations", Tetrahedron, vol. 57, pp. 9199–9223 (2001).
Caddick, "Microwave Assisted Organic Reactions", Tetrahedron, vol. 51, No. 38, pp. 10403–10432 (1995).
Strauss et al., "Invited Review. Developments in Microwave–Assisted Organic Chemistry", Aust. J. Chem., vol. 48, pp. 1665–1692 (1995).
Wang et al., "Synethesis of Aromatic Ethers Without Organic Solvent and Inorganic Carrier Under Microwave Irradiation", Synthetic Communications, vol. 26, No. 2, pp. 301–305 (1996).
Krstenansky et al., "Recent Advances in Microwave–Assisted Organic Syntheses", Current Opinion in Drug Discovery & Development, vol. 3, No. 4, pp. 454–461 (2000).
Bogdal et al., "New Synthetic Method of Aromatic Ethers Under Microwave Irradiation in Dry Media", Synthetic Communications, vol. 28, No. 16, pp. 3029–3039 (1998).
Braga, "Inexpensive Small–Scale Sonochemistry with Magnetic Agitation", J. Chem. Ed., vol. 73, No. 5, pp. A104–A105 (1996).
Kabza et al., "Microwave–Induced Esterification Using Heterogeneous Acid Catalyst in a Low Dielectric Constant Medium", J. Org. Chem., vol. 65, pp. 1210–1214 (2000).

* cited by examiner

Primary Examiner—Alan L. Rotman
Assistant Examiner—Héctor Reyes
(74) Attorney, Agent, or Firm—Paivi Kukkola; John D. Thallemer

(57) ABSTRACT

An accelerated process for preparing a methyl ester having formula (III)

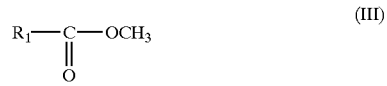

said process comprising reacting a carboxylic acid or salt thereof having formula (I)

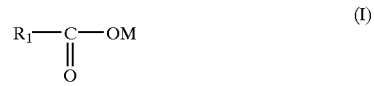

with dimethyl carbonate having formula (II)

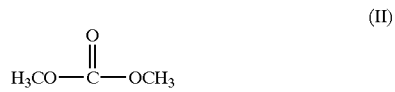

in the presence of a catalyst selected from the group consisting of 1,8-diazabicyclo[5.4.0]undec-7-ene; 1,4-diazabicyclo[2.2.2]octane; 4-dimethylaminopyridine; and combinations thereof, wherein $R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl, and haloalkyl; and M is selected from the group consisting of hydrogen, a monovalent metal, and a monovalent fractional part of a polyvalent metal, wherein said process is conducted under microwave irradiation at a frequency from 300 MHz to 30 GHz, and at a temperature of from about 120° C. to 300° C. for a period of microwave irradiation time from about 1 second to about 300 minutes. The process of the invention is especially advantageous for preparing methyl esters since the process: (1) utilizes an environmentally friendly methylating reagent, dimethylcarbonate; (2) produces a high yield of the methyl ester, generally 95–99% conversion in less than 30 minutes of microwave irradiation; (3) minimizes degradation and/or racemization of optically pure compounds; and (4) minimizes the formation of by-products.

24 Claims, No Drawings

MICROWAVE IRRADIATION PROCESS FOR PREPARING METHYL ESTERS

FIELD OF THE INVENTION

The present invention provides an accelerated process for preparing a methyl ester by reacting a carboxylic acid or salt thereof with dimethyl carbonate in the presence of a catalyst selected from 1,8-diazabicyclo[5.4.0]undec-7-ene (DBU), 1,4-diazabicyclo[2.2.2]octane (DABCO), and 4-dimethylaminopyridine (DMAP), wherein said reaction is conducted under microwave irradiation at a temperature of from about 120° C. to 300° C. for a period of time from about 1 second to about 300 minutes.

BACKGROUND OF THE INVENTION

Methylation of alcohols, amines, carboxylic acids, and activated methylenes is an important process in chemistry. However, due to the environmental and human impact of using toxic and unsafe methylating reagents such as methyl iodide or dimethyl sulfate, the investigation of safer, generally applicable alternatives continues. As an alternative to these toxic methylating agents, dimethyl carbonate has attracted considerable attention for the methylation of phenols, anilines, and activated methylenes. Dimethyl carbonate is non-toxic and generates $CO_2$ and methanol as by-products during methylations. Dimethyl carbonate is also a volatile liquid with a boiling point of 90° C. Hence, the unreacted dimethyl carbonate can be easily recovered by distillation from the reaction mixture and reused.

Microwave irradiation has been used for moisture analysis, organic synthesis, acid decomposition of botanical or biological samples, and rapid hydrolysis of peptides and proteins. Microwave irradiation has also been applied to several organic reactions. Krstenansky et al., *Curr. Opin. Drug Discovery Dev.*, Vol. 3, p. 454 (2000), describes converting alkyl and aryl amides to their corresponding nitrites under microwave irradiation. Wang et al., *Synthetic Communications*, Vol. 26, No. 2, pp. 301–305 (1996), describes using microwave irradiation to synthesize aromatic ethers from phenols and halide in the absence of organic solvent and inorganic carrier. Bogdal et al., *Synthetic Communications*, Vol. 28, No. 16, pp. 3029–3039 (1998), describes reacting phenols with primary alkyl halides under microwave irradiation to synthesize aromatic ethers.

Elder et al., *Journal of Chemical Education*, Vol. 73, No. 5, pp. 104–105 (1996), describes using microwave irradiation to synthesize the following compounds: anthracene, octyl acetate, 2-naphthyl acetate, 2-methoxynaphthalene, and n-phenyl-2,4-dinitroaniline. Kabza et al., *Journal of Organic Chemistry*, Vol. 65, No. 4, pp. 1210–1214 (2000), describes using microwave irradiation in the acid-catalyzed Fisher-type esterification of isopentyl alcohol and acetic acid. Kabza concluded that the esterification reaction behaved comparably under both microwave and thermal conditions. Caddick, *Tetrahedron*, Vol. 51, No. 38, pp. 10403–10432 (1995), describes microwave assisted organic reactions. Such organic reactions described are: pericyclic, cyclization, aromatic substitution, oxidation, catalytic transfer hydrogenation, alkene functionalization, alkylation, decarboxylation, carbohydrates, radical reactions, protecting groups, condensation, peptide synthesis, silicon, and rearrangement. Perreux et al., *Tetrahedron*, Vol. 57, pp. 9199–9223 (2001), describes microwave effects in organic synthesis. Such organic syntheses include bimolecular reactions between neutral reactants, bimolecular reactions with one charged reactant, unimolecular reactions.

U.S. Pat. No. 4,513,146 describes a method for producing esters from highly hindered carboxylic acids and carbonates. The method involves reacting the highly hindered carboxylic acid with a carbonate with or without a catalyst at a temperature of 175° C. According to the only example, the reaction took 4 hours and 50 minutes. U.S. Pat. No. 4,513,146 states that exemplary bases are nitrogen-containing heterocyclic catalysts such as pyridine, 4-(dimethylamino) pyridine, imidazole, 2,6-lutidine, and 2,4,6-collidine.

U.S. Pat. No. 5,278,333 describes a process for preparing α-phenylmethylpropionate by reacting a mixture of phenylacetic acid, dimethyl carbonate, and potassium carbonate in a molar ratio of 1:20:2, respectively, in an autoclave at a temperature of 225° C. for 15 hours.

It would be advantageous from a production standpoint to develop an accelerated process for preparing methyl esters which utilizes dimethyl carbonate as a reactant. In addition, the process should minimize degradation and/or racemization of optically pure compounds, and minimize the formation of by-products.

SUMMARY OF THE INVENTION

The invention provides an accelerated process for preparing a methyl ester having formula (III)

(III)

said process comprising reacting a carboxylic acid or salt thereof having formula (I)

(I)

with dimethyl carbonate having formula (II)

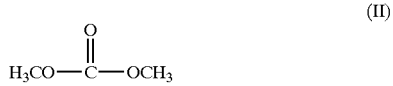

(II)

in the presence of a catalyst selected from the group consisting of 1,8-diazabicyclo[5.4.0]undec-7-ene; 1,4-diazabicyclo[2.2.2]octane; 4-dimethylaminopyridine; and combinations thereof, wherein $R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl, and haloalkyl; and M is selected from the group consisting of hydrogen, a monovalent metal, and a monovalent fractional part of a polyvalent metal, wherein said process is conducted under microwave irradiation at a frequency from 300 MHz to 30 GHz, and at a temperature of from about 120° C. to 300° C. for a period of microwave irradiation time from about 1 second to about 300 minutes.

According to another aspect, the invention provides a compound having formula (III)

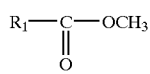

(III)

wherein said compound is prepared by an accelerated process comprising reacting a carboxylic acid or salt thereof having formula (I)

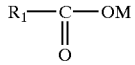

(I)

with dimethyl carbonate having formula (II)

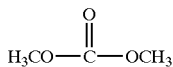

(II)

in the presence of a catalyst selected from the group consisting of 1,8-diazabicyclo[5.4.0]undec-7-ene; 1,4-diazabicyclo[2.2.2]octane; 4-dimethylaminopyridine; and combinations thereof, wherein $R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl, and haloalkyl; and M is selected from the group consisting of hydrogen, a monovalent metal, and a monovalent fractional part of a polyvalent metal, wherein said process is conducted under microwave irradiation at a frequency from 300 MHz to 30 GHz, and at a temperature of from about 120° C. to 300° C. for a period of microwave irradiation time from about 1 second to about 300 minutes.

The process of the invention is especially advantageous for preparing methyl esters since the process: (1) utilizes an environmentally friendly methylating reagent, dimethylcarbonate; (2) produces a high yield of the methyl ester, generally 95–99% conversion in less than 30 minutes of microwave irradiation; (3) minimizes degradation and/or racemization of optically pure compounds; and (4) minimizes the formation of by-products.

DESCRIPTION OF THE INVENTION

The accelerated process of the invention for preparing a methyl ester utilizes microwave irradiation. The microwave region of the electromagnetic spectrum corresponds to wavelengths from 1 cm to 1 m and frequencies from 300 MHz to 30 GHz. By International Convention, however, domestic and industrial microwave ovens generally operate at greater than 900 MHz, preferably about 2450 MHz to about 2455 MHz, in order to prevent interference with RADAR transmissions and telecommunications. Thus, the entire microwave region is not readily available for heating applications. Sources of microwave irradiation include multimode ovens and monomode ovens which may be batch or continuous devices. A preferred monomode oven is a continuous-flow reactor, such as a Milestone ETHOS-CFR continuous-flow reactor.

The methyl ester has formula (III)

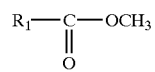

(III)

in formula (III), $R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl, and haloalkyl. The reaction is conducted in the presence of a catalyst which is selected from 1,8-diazabicyclo[5.4.0]undec-7-ene (DBU); 1,4-diazabicyclo[2.2.2]octane (DABCO); and 4-dimethylaminopyridine (DMAP). A combination of catalysts may also be used.

The process of the invention involves reacting a carboxylic acid or salt thereof having formula (I)

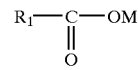

(I)

with dimethyl carbonate having formula (II)

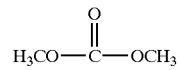

(II)

in formula (I), $R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl, and haloalkyl, and M is selected from the group consisting of hydrogen, a monovalent metal, and a monovalent fractional part of a polyvalent metal. The metal is preferably selected from sodium, potassium, magnesium, or calcium.

As used herein, "alkyl" means straight chain or branched alkyl, which may be, for example, $C_1$–$C_{10}$-alkyl such as methyl, ethyl, n-propyl, isopropyl, n-butyl, isobutyl, sec-butyl, tert-butyl, straight or branched pentyl, straight or branched hexyl, straight or branched heptyl, straight or branched nonyl or straight or branched decyl. Preferably alkyl is $C_1$–$C_4$-alkyl.

"Aryl" means $C_6$–$C_{14}$-aryl, preferably $C_6$–$C_{10}$-aryl, and may be, for example, substituted by at least one group selected from mercapto, dialkylamino, nitro, alkoxy, halogen, keto, cyano, or a combination. Preferably aryl is phenyl.

"Alkoxy" means straight chain or branched alkoxy and may be, for example, $C_1$–$C_{10}$-alkoxy such as methoxy, ethoxy, n-propoxy, isopropoxy, n-butoxy, isobutoxy, sec-butoxy, tert-butoxy, or straight or branched pentoxy, hexyloxy, heptyloxy, octyloxy, nonyloxy or decyloxy. Preferably alkoxy is $C_1$–$C_4$-alkoxy.

"Alkenyl" means straight chain or branched alkenyl, which may be, for example, $C_2$–$C_{10}$ alkenyl such as vinyl, 1-propenyl, 2-propenyl, 1-butenyl, isobutenyl, or straight or branched pentenyl, hexenyl, heptenyl, octenyl, nonenyl or decenyl. Preferred alkenyl is $C_2$–$C_4$-alkenyl.

"Cycloalkyl" means $C_3$–$C_{10}$-cycloalkyl having 3- to 8-ring carbon atoms and may be, for example, cyclopropyl, cyclobutyl, cyclopentyl, cyclohexyl, cycloheptyl or cycloheptyl, any of which can be substituted by one, two or more $C_1$–$C_4$-alkyl groups, particularly methyl groups. Preferably, cycloalkyl is $C_3$–$C_6$-cycloalkyl.

"Benzocycloalkyl" means cycloalkyl (e.g., one of the $C_3$–$C_{10}$-cycloalkyl groups mentioned hereinbefore), attached at two adjacent carbon atoms to a benzene ring. Preferably, benzocycloalkyl is benzo-$C_5$–$C_6$-cycloalkyl, especially benzocyclohexyl (tetrahydronaphthyl).

"Cycloalkylalkyl" means $C_3$–$C_{10}$-cycloalkyl-$C_1$–$C_{10}$-alkyl where the $C_3$–$C_{10}$-cycloalkyl group has 3- to 8-ring carbon atoms and may be, for example, one of the $C_1$–$C_{10}$-alkyl groups mentioned hereinbefore, particularly one of the $C_1$–$C_4$-alkyl groups, substituted by one of the $C_3$–$C_{10}$-cycloalkyl groups mentioned hereinbefore. Preferably cycloalkylalkyl is $C_3$–$C_6$-cycloalkyl-$C_1$–$C_4$-alkyl.

"Aralkyl" means straight chain or branched $C_6$–$C_{10}$-aryl-$C_1$–$C_{10}$-alkyl and may be, for example, one of the $C_1$–$C_{10}$-alkyl groups mentioned hereinbefore, particularly one of the $C_1$–$C_4$-alkyl groups, substituted by phenyl, tolyl, xylyl or naphthyl. Preferably, aralkyl is phenyl-$C_1$–$C_4$-alkyl, particularly benzyl or 2-phenylethyl.

"Heterocyclic" means a monovalent heterocyclic group having up to 20 carbon atoms and one, two, three or four heteroatoms selected from nitrogen, oxygen and sulfur, the group optionally having an alkyl, alkylcarbonyl, hydroxyalkyl, alkoxyalkyl or aralkyl group attached to a ring carbon or nitrogen atom and being linked to the remainder of the molecule through a ring carbon atom, and may be, for example, a group, preferably a monocyclic group, with one nitrogen, oxygen or sulfur atom such as pyrryl, pyridyl, piperidyl, furyl, tetrahydrofuryl or thienyl, or a group, preferably a monocyclic group, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Preferably, heterocyclic is a monocyclic group having 5- or 6-ring atoms and one or two nitrogen atoms, or one nitrogen atom and one oxygen atom, in the ring and optionally substituted on a ring nitrogen atom by $C_1$–$C_4$-alkyl, hydroxy-$C_1$–$C_4$-alkyl, $C_1$–$C_4$-alkylcarbonyl or phenyl-$C_1$–$C_4$-alkyl.

"Heteroaralkyl" means straight chain or branched aralkyl (e.g., one of the $C_6$–$C_{10}$-aryl-$C_1$–$C_{10}$-alkyl groups mentioned hereinbefore) substituted by one or more heterocyclic groups.

"Alkoxyalkyl" means straight chain or branched alkyl substituted by one or more alkoxy groups and may be, for example, a $C_1$–$C_{10}$-alkoxy-$C_1$–$C_{10}$-alkyl group, such as one of the $C_1$–$C_{10}$-alkyl groups, particularly one of the $C_1$–$C_4$-alkyl groups, mentioned hereinbefore substituted by one of the $C_1$–$C_{10}$-alkoxy groups, preferably one of the $C_1$–$C_4$-alkoxy groups, mentioned hereinbefore. Preferably alkoxyalkyl is $C_1$–$C_4$-alkoxy-$C_1$–$C_4$-alkyl.

"Carboxyalkyl" means straight chain or branched alkyl, for example, $C_1$–$C_{10}$-alkyl such as one of the $C_1$–$C_{10}$-alkyl groups mentioned hereinbefore, substituted, preferably on a primary carbon atom, by a carboxyl group. Preferably carboxyalkyl is carboxy-$C_1$–$C_4$-alkyl.

"Alkylcarbonyl" means a group $R_2C\!\!=\!\!O$ wherein $R_2$ is alkyl, for example, $C_1$–$C_{10}$-alkyl such as one of the $C_1$–$C_{10}$-, preferably $C_1$–$C_4$-, alkyl groups mentioned hereinbefore. Preferably, alkylcarbonyl is $C_1$–$C_4$-alkylcarbonyl, for example, $R_2C\!\!=\!\!O$ wherein $R_2$ is $C_1$–$C_4$-alkyl.

"Alkoxycarbonyl" means a group $R_3CO$ wherein $R_3$ is an alkoxy group, for example, a $C_1$–$C_{10}$-alkoxy group such as one of the $C_1$–$C_{10}$, preferably $C_1$–$C_4$, alkoxy groups mentioned hereinbefore. Preferably, alkoxycarbonyl is $C_1$–$C_4$-alkoxycarbonyl, for example, $R_3CO$ wherein $R_3$ is $C_1$–$C_4$-alkoxy.

"Alkoxycarbonylalkyl" means straight or branched chain alkyl, for example, a $C_1$–$C_{10}$-alkyl group such as one of the $C_1$–$C_{10}$-, preferably $C_1$–$C_4$-, alkyl groups mentioned hereinbefore, substituted by an alkoxycarbonyl group as hereinbefore defined. Preferably, alkoxycarbonylalkyl is $C_1$–$C_4$-alkoxy-carbonyl-$C_1$–$C_4$-alkyl.

"Haloalkyl" means straight chain or branched alkyl, for example, $C_1$–$C_{10}$-alkyl such as one of the $C_1$–$C_{10}$-alkyl groups mentioned hereinbefore, substituted by one or more, for example one, two or three, halogen atoms, preferably fluorine or chlorine atoms. Preferably haloalkyl is $C_1$–$C_4$-alkyl substituted by one, two or three fluorine or chlorine atoms.

Specific examples of carboxylic acids of formula (I) are 2,6-dimethoxybenzoic acid, 2,3:4,6-di-O-isopropylidene-α-L-xylo-2-hexulofuranosonate monohydrate, N-α-t-boc-L-proline, benzoic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, 2,2-dimethylpropanoic acid, 2,2-dimethylbutanoic acid, 2,2-dimethyloctanoic acid, and the sodium and potassium salts thereof. A combination of carboxylic acids may also be used. Preferably the carboxylic acid is selected from 2,6-dimethoxybenzoic acid, 2,3:4,6-di-O-isopropylidene-α-L-xylo-2-hexulofuranosonate monohydrate, N-α-t-boc-L-proline, and benzoic acid.

The process of the invention is preferably conducted in the liquid phase. It may be carried out in the form selected from batch, continuous, semibatch, or semicontinuous. Dimethyl carbonate is a liquid under the conditions of the reaction and it may act as a solvent for the carboxylic acid or salt thereof. Typically, but not necessarily, excess dimethyl carbonate is employed relative to the amount of carboxylic acid or salt thereof, and this usually serves to dissolve the carboxylic acid or salt thereof throughout the reaction. Although extrinsic solvent is not ordinarily employed, it may be used when desired or when necessary to dissolve one or more of the reactants. Examples of suitable extrinsic solvents include: acetonitrile, ethyl acetate, acetone, tetrahydrofuran, heptane, cyclohexane, t-butyl methyl ether, dimethy sulfoxide, toluene, dioxane, dimethylformamide and chlorinated solvents such as chloroform, methylene chloride, ethylene chloride, and chlorobenzene. A preferred extrinsic solvent is acetonitrile. A combination of solvents may also be used.

The process of the invention is conducted at a temperature of from about 120° C. to about 300° C., preferably, about 140° C. to about 250° C.; and more preferably from about 150° C. to about 200° C. Most preferably, the process is conducted at a temperature of about 160° C. The pressure of the reaction depends upon the temperature of the reaction, and the boiling point of the reactants and solvent. The present inventors have determined that a higher reaction temperature may require higher pressure in order to prevent boiling of either the reactants or solvent. Generally, the process is conducted under a pressure of from about 1 bar to about 60 bar, preferably, from about 10 bar to about 35 bar, most preferably about 20 bar.

The process of the invention is conducted for a period of microwave irradiation time sufficient to form a methyl ester. Preferably, the period of microwave irradiation time is from about 1 second to about 300 minutes, more preferably from about 5 minutes to about 30 minutes. Most preferably, the process of the invention is conducted for a period of microwave irradiation time from 6 minutes to 25 minutes.

The equivalent ratio of the catalyst to the carboxylic acid or salt thereof initially present may vary widely, but preferably is in the range of from about 0.01:1 to about 2:1. More preferably, the equivalent ratio of the catalyst to the carboxylic acid or salt thereof initially present is from about 0.1:1 to about 1:1, most preferably, about 1:1.

In one embodiment of the invention, an amine base is used in the process of the invention to prepare a methyl ester. Preferred amine bases are trialkylamines and ethylenediamines. Specific amine bases include, but are not limited to, triethylamine, N,N-diisopropylethylamine and N,N'-diisopropylethylenediamine. A combination of amine bases may also be used.

Following preparation, the methyl ester may be recovered from the reaction mixture by any of the various techniques known to the art. A preferred method of recovering the methyl ester involves treating the reaction mixture in sequence with an acid solution and a basic solution, followed by distillation of any organic solvent and dimethyl carbonate.

The following non-limiting examples illustrate further aspects of the invention.

EXAMPLE 1

Preparation of methyl 2,6-dimethoxybenzoate

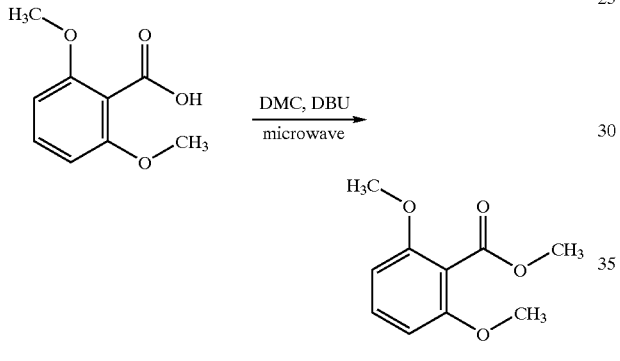

A solution containing 2,6-dimethoxybenzoic acid (5.0 g, 27.5 mmol), DBU (4.2 g, 27.5 mmol), DMC (50 mL), and acetonitrile (50 mL) was circulated at 20 mL/min by a pump through a Milestone ETHOS-CFR continuous-flow reactor, which had been preheated to 160° C. at 20 bar by microwave irradiation. The reaction mixture was analyzed by HPLC after each cycle (6 minutes microwave irradiation). The yield of methyl 2,6-dimethoxybenzoate after two cycles (12 minutes microwave irradiation time) as determined by HPLC was 99% conversion. The reaction mixture was concentrated under vacuum. The residue was diluted with EtOAc (100 mL) and H$_2$O (80 mL). The organic layer was separated and washed in sequence with H$_2$O (80 mL), 2 M HCl (2×80 mL), saturated aqueous NaHCO$_3$ (2×80 mL), and H$_2$O (2×80 mL). The organic layer was dried over Na$_2$SO$_4$, filtered, and concentrated under vacuum to give methyl 2,6-dimethoxybenzoate (5.16 g, 85% isolated yield) as a white solid.

EXAMPLE 2

Preparation of methyl phenylacetate

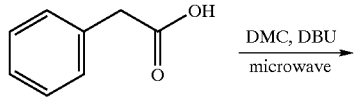

-continued

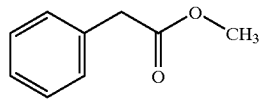

A solution containing phenylacetic acid (5.0 g, 36.7 mmol), DBU (6 g, 36.7 mmol), DMC (50 mL), and acetonitrile (50 mL) was circulated at 20 mL/min by a pump through a Milestone ETHOS-CFR continuous-flow reactor, which had been preheated to 160° C. at 20 bar by microwave irradiation. The reaction mixture was analyzed by HPLC after each cycle (6 minutes microwave irradiation). The yield of methyl phenylacetate after two passes (12 minutes microwave irradiation time) as determined by HPLC was 98% conversion. The reaction mixture was concentrated under vacuum. The residue was diluted with EtOAc (80 mL) and H$_2$O (80 mL). The organic layer was separated and washed in sequence with H$_2$O (80 mL), 2 M HCl (2×80 mL), saturated aqueous NaHCO$_3$ (2×80 mL), and H$_2$O 80 mL). The organic layer was dried over Na$_2$SO$_4$, filtered, and concentrated under vacuum to give methyl phenylacetate (5.31 g, 96% isolated yield) as a liquid.

EXAMPLE 3

Preparation of N-α-t-Boc-L-proline methyl ester

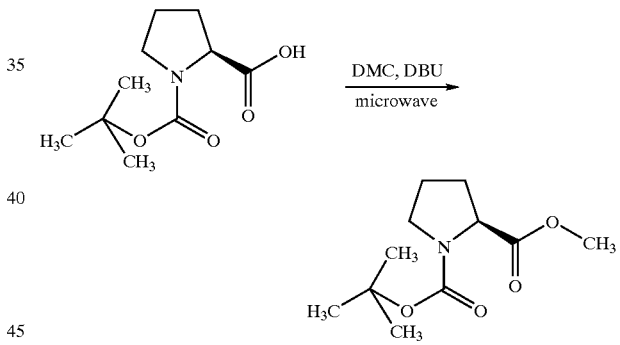

A solution containing N-α-t-Boc-L-proline (5.0 g, 23.3 mmol), DBU (3.54 g, 23.3 mmol), DMC (50 mL), and acetonitrile (50 mL) was circulated at 20 mL/min by a pump through a Milestone ETHOS-CFR continuous-flow reactor, which had been preheated to 160° C. at 20 bar by microwave irradiation. The reaction mixture was analyzed by HPLC after each cycle (6 minutes microwave irradiation). The yield of N-α-t-Boc-L-proline methyl ester after two cycles (12 minutes microwave irradiation time) as determined by HPLC was 99% conversion. The reaction mixture was concentrated under vacuum. The residue was diluted with EtOAc (80 mL) and H$_2$O (80 mL). The organic layer was separated and washed in sequence with H$_2$O (80 mL), 10% aqueous citric acid (2×80 mL), saturated aqueous NaHCO$_3$ (2×80 mL), and H$_2$O (2×80 mL). The organic layer was dried over Na$_2$SO$_4$, filtered, and concentrated under vacuum to give N-α-t-Boc-L-proline methyl ester (5.04 g, 95% isolated yield) as an oil.

EXAMPLE 4

Preparation of methyl 2,3:4,6-di-O-isopropylidene-α-L-xylo-2-hexulofuranosonate

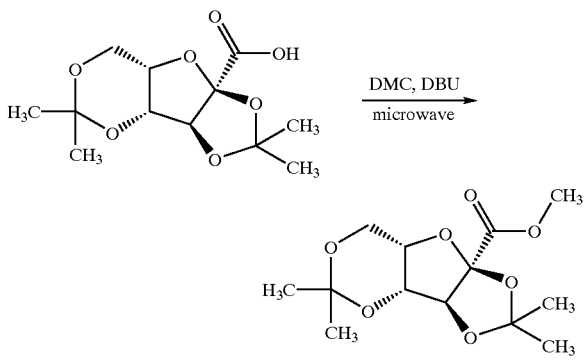

2,3:4,6-di-O-isopropylidene-α-L-xylo-2-hexulofuranosonic acid monohydrate (8.0 g, 29.1 mmol) was dissolved into acetonitrile (100 mL). The resulting solution was concentrated to dryness under vacuum. The residue was dissolved into acetonitrile (100 mL) and concentrated to dryness under vacuum once more to remove any water present. The residue was then dissolved into a solution containing DBU (4.4 g, 29.1 mmol), DMC (80 mL), and acetonitrile (80 mL). The resulting solution was circulated at 20 mL/min by a pump through a Milestone ETHOS-CFR continuous-flow reactor, which had been preheated to 160° C. at 20 bar by microwave irradiation. The reaction mixture was analyzed by HPLC after each cycle (6 minutes microwave irradiation). The yield of methyl 2,3:4,6-di-O-isopropylidene-α-L-xylo-2-hexulofuranosonate after four cycles (24 minutes microwave irradiation time) as determined by HPLC was 95% conversion. The reaction mixture was concentrated under vacuum. The residue was diluted with EtOAc (90 mL) and H$_2$O (90 mL). The organic layer was separated and washed in sequence with H$_2$O (90 mL), 10% aqueous citric acid (2×90 mL), saturated aqueous NaHCO$_3$ (2×90 mL), and H$_2$O (2×80 mL). The organic layer was dried over Na$_2$SO$_4$, filtered, and concentrated under vacuum to give methyl 2,3:4,6-di-O-isopropylidene-α-L-xylo-2-hexulofuranosonate (6.71 g, 80% isolated yield) as an oil.

EXAMPLE 5

Preparation of methyl benzoate

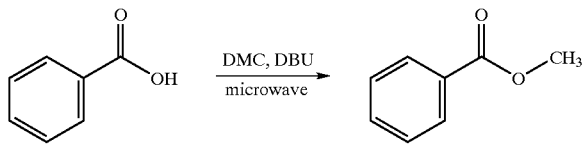

A solution containing benzoic acid (50.0 g, 410 mmol), DBU (62.5 g, 410 mmol), DMC (250 mL), and acetonitrile (250 mL) was circulated at 20 mL/min by a pump through a Milestone ETHOS-CFR continuous-flow reactor, which had been preheated to 160° C. at 20 bar by microwave irradiation. The reaction mixture was analyzed by HPLC after each cycle (6 minutes microwave irradiation). The yield of methyl benzoate after 3 cycles (18 minutes microwave irradiation time) as determined by HPLC was 98% conversion. The reaction mixture was concentrated under vacuum. The residue was diluted with EtOAc (400 mL) and H$_2$O (300 mL). The organic layer was separated and washed in sequence with H$_2$O (300 mL), 2 M HCl (2×200 mL), saturated aqueous NaHCO$_3$ (2×200 mL), and H$_2$O (1×200 mL). The organic layer was dried over Na$_2$SO$_4$, filtered, and concentrated under vacuum to give methyl benzoate (47.8 g, 86% isolated yield) as a liquid.

The process of the invention is especially advantageous for preparing methyl esters since the process: (1) utilizes an environmentally friendly methylating reagent, dimethylcarbonate; (2) produces a high yield of the methyl ester, generally 95–99% conversion in less than 30 minutes of microwave irradiation; (3) minimizes degradation and/or racemization of optically pure compounds; and (4) minimizes the formation of by-products.

While the invention has been described with particular reference to certain embodiments thereof, it will be understood that changes and modifications may be made by those of ordinary skill within the scope and spirit of the following claims:

What is claimed is:

1. An accelerated process for preparing a methyl ester having formula (III)

(III)

said process comprising reacting a carboxylic acid or salt thereof having formula (I)

(I)

with dimethyl carbonate having formula (II)

(II)

in the presence of a catalyst selected from the group consisting of 1,8-diazabicyclo[5.4.0]undec-7-ene; 1,4-diazabicyclo[2.2.2]octane; 4-dimethylaminopyridine; and combinations thereof, wherein R$_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl, and haloalkyl; and M is selected from the group consisting of hydrogen, a monovalent metal, and a monovalent fractional part of a polyvalent metal, wherein said process is conducted under microwave irradiation at a frequency from 300 MHz to 30 GHz, and at a temperature of from about 120° C. to 300° C. for a period of microwave irradiation time from about 1 second to about 300 minutes.

2. The process according to claim 1 wherein M is selected from the group consisting of hydrogen, sodium, potassium, magnesium, and calcium.

3. The process according to claim 2 wherein M is hydrogen.

4. The process according to claim 1 wherein R$_1$ is substituted by at least one group which is selected from the group consisting of mercapto, dialkylamino, nitro, alkoxy, halogen, keto, cyano, and combinations thereof.

5. The process according to claim 4 wherein $R_1$ is substituted by at least one group which is selected from the group consisting of dialkylamino, alkoxy, and halogen.

6. The process according to claim 1 wherein the carboxylic acid is selected from the group consisting of 2,6-dimethoxybenzoic acid, 2,3:4,6-di-O-isopropylidene-α-L-xylo-2-hexulofuranosonate monohydrate, N-α-t-boc-L-proline, benzoic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, 2,2-dimethylpropanoic acid, 2,2-dimethylbutanoic acid, 2,2-dimethyloctanoic acid, and the sodium and potassium salts thereof.

7. The process according to claim 6 wherein the carboxylic acid is selected from the group consisting of 2,6-dimethoxybenzoic acid, 2,3:4,6-di-O-isopropylidene-α-L-xylo-2-hexulofuranosonate monohydrate, N-α-t-boc-L-proline, and benzoic acid.

8. The process according to claim 1 which is conducted in the presence of an extrinsic solvent.

9. The process according to claim 8 wherein the extrinsic solvent is selected from the group consisting of acetonitrile, ethyl acetate, acetone, benzene, toluene, dioxane, dimethylformamide, chloroform, methylene chloride, ethylene chloride, carbon tetrachloride, chlorobenzene, and combinations thereof.

10. The process according to claim 9 wherein the extrinsic solvent is acetonitrile.

11. The process according to claim 1 wherein the temperature is from about 140° C. to about 250° C.

12. The process according to claim 11 wherein the temperature is from about 150° C. to 200° C.

13. The process according to claim 12 wherein the temperature is about 160° C.

14. The process according to claim 1 wherein the period of microwave irradiation time is from about 5 minutes to about 30 minutes.

15. The process according to claim 14 wherein the period of microwave irradiation time is from about 6 minutes to about 25 minutes.

16. The process according to claim 1 wherein the equivalent ratio of the catalyst to the carboxylic acid or salt thereof initially present is from 0.01:1 to 2:1.

17. The process according to claim 16 wherein the equivalent ratio of the catalyst to the carboxylic acid or salt thereof initially present is from 0.1:1 to 1:1.

18. The process according to claim 1 which further comprises an amine base.

19. The process according to claim 18 wherein the amine base is selected from the group consisting of triethylamine, N,N-diisopropylethylamine and N,N'-diisopropylethylenediamine.

20. The process according to claim 1 wherein the sources of microwave irradiation is selected from the group consisting of a multimode oven, monomode oven, and combinations thereof.

21. The process according to claim 1 wherein the frequency of the microwave irradiation is from 900 MHz to 3000 MHz.

22. The process according to claim 21 wherein the frequency of the microwave irradiation is from about 2450 MHz to about 2455 MHz.

23. The process according to claim 1 wherein the process is carried out by a form selected from the group consisting of batch, continuous, semibatch, and semicontinuous.

24. An accelerated process for preparing a methyl ester having formula (VI)

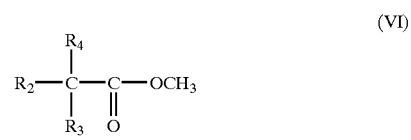

(VI)

said process comprising reacting a carboxylic acid or salt thereof having formula (IV)

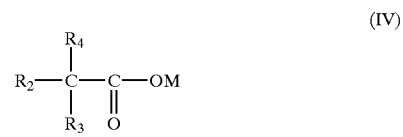

(IV)

with dimethyl carbonate having formula (V)

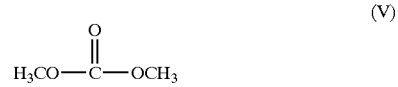

(V)

in the presence of a catalyst selected from the group consisting of 1,8-diazabicyclo[5.4.0]undec-7-ene; 1,4-diazabicyclo[2.2.2]octane; 4-dimethylaminopyridine; and combinations thereof, wherein $R_2$, $R_3$ and $R_4$, are independently selected from the group consisting of hydrogen, alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl, and haloalkyl; and M is selected from the group consisting of hydrogen, a monovalent metal, and a monovalent fractional part of a polyvalent metal, wherein said process is conducted under microwave irradiation at a frequency from 300 MHz to 30 GHz, and at a temperature of from about 120° C. to 300° C. for a period of microwave irradiation time from about 1 second to about 300 minutes.

* * * * *